United States Patent
Stevenson et al.

(10) Patent No.: US 7,470,735 B2
(45) Date of Patent: Dec. 30, 2008

(54) PHENOL-FREE PHOSPHITES

(75) Inventors: Donald R. Stevenson, Dover, OH (US);
Duong N. Nguyen, Dover, OH (US);
Mark E. Harr, New Philadelphia, OH (US); Michael R. Jakupca, Canton, OH (US)

(73) Assignee: Dover Chemical Corporation, Dover, OH (US)

( * ) Notice: Subject to any disclaimer, the term of this patent is extended or adjusted under 35 U.S.C. 154(b) by 276 days.

(21) Appl. No.: 10/709,578

(22) Filed: May 14, 2004

(65) Prior Publication Data

US 2004/0180999 A1 Sep. 16, 2004

Related U.S. Application Data

(63) Continuation-in-part of application No. 10/709,510, filed on May 11, 2004, now Pat. No. 7,320,764, which is a continuation-in-part of application No. 10/086,619, filed on Mar. 1, 2002, now Pat. No. 6,824,711.

(60) Provisional application No. 60/315,746, filed on Aug. 29, 2001, provisional application No. 60/314,181, filed on Aug. 16, 2001, provisional application No. 60/273,303, filed on Mar. 2, 2001.

(51) Int. Cl.
*C08K 5/524* (2006.01)
(52) U.S. Cl. ........................ 524/147; 524/115; 524/151
(58) Field of Classification Search .................. 524/115, 524/147, 151; 558/70
See application file for complete search history.

(56) References Cited

U.S. PATENT DOCUMENTS

| | | | |
|---|---|---|---|
| 3,047,608 A | 7/1962 | Friedman et al. | |
| 3,205,250 A | 9/1965 | Hechenbleikner | |
| 3,281,381 A | 10/1966 | Hechenbleikner | |
| 4,206,103 A | 6/1980 | Kromolicki et al. | |
| 4,290,976 A | 9/1981 | Hechenbleikner | |
| 6,362,260 B1 | 3/2002 | Stevenson et al. | |
| 6,824,711 B2 * | 11/2004 | Stevenson et al. | 252/400.24 |
| 2003/0001136 A1 * | 1/2003 | Stevenson et al. | 252/299.1 |
| 2004/0164279 A1 * | 8/2004 | Stevenson et al. | 252/397 |
| 2004/0183054 A1 * | 9/2004 | Stevenson et al. | 252/400.24 |
| 2004/0186207 A1 * | 9/2004 | Krohnke | 524/115 |

FOREIGN PATENT DOCUMENTS

| | | | |
|---|---|---|---|
| JP | 49-20928 | * | 5/1974 |
| JP | 74020928 B | | 5/1974 |

OTHER PUBLICATIONS

Derwent abstract for JP 74-020928 (corresponds to JP 49-20928).*

* cited by examiner

*Primary Examiner*—Kriellion A Sanders
(74) *Attorney, Agent, or Firm*—Louis F. Wagner; Hahn Loeser + Parks LLP

(57) ABSTRACT

Various phenol-free phosphites for use in PVC as an alternative to the conventional phenol-containing products phenyl diisodecyl phosphite and diphenyl isodecyl phosphite were tested. These phosphites utilize para-cumyl phenol-based derivatives in order to provide a phenol free derivative of the above mentioned conventional phosphites.

23 Claims, 7 Drawing Sheets ns with phenol is based on the use of vinyl chloride polymers
PHENOL-FREE PHOSPHITES This invention claims priority to U.S. patent application Ser. No. 10/709,510, filed May 11, 2004, now U.S. Pat. No. 7,320,764 which is a continuation-in-part of U.S. patent application Ser. No. 10/086,619, filed Mar. 1, 2002, now U.S. Pat. No. 6,824,711 which is a non-provisional patent application of U.S. Provisional Patent Application Ser. No. 60/315,746 filed on Aug. 29, 2001 and United States Provisional Patent Application Ser. No. 60/314,181 filed on Aug. 16, 2001 and U.S. Provisional Patent Application Ser. No. 60/273,303 filed on Mar. 2, 2001.

BACKGROUND OF INVENTION

The invention relates to phenol-free phosphites, which can be used to stabilize organic polymers, especially polyvinyl chloride ("PVC").

Liquid organic phosphites have been used for many years alone and in combination with mixed metal stabilizers for the stabilization of vinyl halide polymers, especially PVC. The Encyclopedia of PVC, Volume 1, L. Nass, Ed., Marcel Dekker Inc., New York, 1977. The phosphite esters employed may be trialkyl, triaryl, mixed alkyl/aryl, and even polymeric.

The problem of imparting polyvinyl chloride with sufficient heat processing stability at temperatures at which the polymer becomes sufficiently fluid or softened to permit shaping is of course of long standing, and has been satisfactorily resolved by the addition to the polymer of various combinations of known heat stabilizers. At processing temperatures, the PVC resin can degrade, liberating hydrogen chloride, discolor, become brittle, and stick to the processing equipment. These problems are overcome by combining with the polymer before heat processing or during heat processing, one or more of the well established and conventional heat stabilizers, such as, for example, alkyl tin mercaptides or barium/cadmium or barium/zinc or calcium/zinc salt mixed metal stabilizers, aryl, alkyl and mixed aryl/alkyl phosphites, or combinations of the above.

These stabilizers, in preventing the deterioration of the polymers during processing at high temperatures, also permit manufacture of products with increased intrinsic quality because of the enhancement of their resistance to thermal and light degradation during use. In addition, because of the ability of these products to withstand more rigorous conditions, their versatility is increased and new areas of application are thereby opened. Without going into details or theory, it has been found that mixed alkyl/aryl phosphites such as diphenylisodecyl phosphite and phosphites based on pentaerythritol give the best overall performance in combination with mixed metal stabilizer systems for the stabilization of PVC.

In recent years there has been much concern with exposure to volatiles from the processing of PVC resin, and the exposure to volatiles from articles shaped from stabilized PVC resin exposed to elevated use temperatures. The volatilization of one or more components, or of the decomposition products therefrom, cause the condensation of these volatile components as "fog" on surfaces adjacent to the PVC articles. It has been found that one of the volatiles from the processing of PVC containing certain stabilizers is phenol. The phenol comes from the phosphite used in combination with the mixed metal stabilizer. There is a great need to eliminate or at least minimize the phenol content of phosphite stabilizers and still have a stabilizer which gives good color and processing stability and is relatively inexpensive.

One important objection to the contamination of PVC resins with phenol is based on the use of vinyl chloride polymers in food applications, e.g. in the manufacture of food containers. The use of phenol-free stabilizers prevents the transfer of objectionable odors or materials to food. Another consideration is the fact that for other applications, phenol has been identified as the source of the cause of premature discoloration, and is a water-soluble component.

A preferred phosphite for use with mixed metal stabilizers is diphenyl isodecyl phosphite, but this stabilizer contains about 50% of total phenol. Other phosphite stabilizers based on dialkyl pentaerythritol diphosphites have been known for some time as effective stabilizers for vinyl polymers. Despite wide usage as stabilizers for vinyl chloride polymers, polyolefins, polyurethanes, styrene polymers, and ABS, this type of phosphite has not been entirely satisfactory. The reason for this is the fact that, because of the method of preparation, namely by transesterification from triphenyl phosphite, the dialkyl pentaerythritol diphosphite is contaminated with phenol. Also, pentaerythritol phosphites are prone to hydrolysis that liberate solid pentaerythritol. In addition, it is advantageous to use mixed metal/phosphite stabilizer combinations as a single liquid component added to the PVC resin during processing. The dialkyl pentaerythritol diphosphites mentioned above are not easily combined with the liquid mixed metal stabilizers, and on standing, a mixture of the liquid mixed metal stabilizer and the dialkyl or diaryl pentaerythritol diphosphite separate into a lighter liquid layer and a more solid layer of heavy sludge. The dialkyl or diaryl pentaerythritol diphosphite also has a tendency to separate from the PVC matrix on compounding, causing a phenomenon known as plate-out. This lack of package stability and formation of plate-out greatly reduces the usefulness of this type of phosphite.

It is also known that trialkyl phosphites, while providing good early stability and color as well as good initial ultraviolet stability, suffer from poor long-term stability. Triaryl phosphites by contrast, provide good long-term stability, but suffer from early color and ultraviolet stability. Bis-phenol A diphosphites are recognized to provide excellent performance, but at a cost which is higher than commercially viable for many applications.

Pentaerythritol type phosphites and vinyl resins stabilized with such phosphites are disclosed in U.S. Pat. No. 3,281,381 by I. Hechenbleikner and F. C. Lanoue. These pentaerythritol phosphites are prepared by the transesterification of triphenyl phosphite with pentaerythritol to give, depending on the molar ratio of the triphenyl phosphite and pentaerythritol, a variety of possible structures. Tetra-phosphites are made by using four (4) moles of the tri(aromatic phosphite), such as triphenyl phosphite for each mole of the pentaerythritol. "Spiro" products, which are diphosphites, are made from the reaction of two moles of the triaryl phosphite with one mole of pentaerythritol. Mixed cyclic and non-cyclic esters are made by the reaction of three moles of the starting phosphite with each mole of pentaerythritol. Although the phenol formed in the transesterification reaction used to produce these materials from triphenylphosphite is removed by distillation during the preparation, the products still contain small quantities of free phenol, and phenol bound as a phosphite ester may be liberated during compounding or mixing.

Hechenbleikner, in U.S. Pat. No. 3,205,250 suggests the use of dialkylpentaerythritol diphosphites as stabilizers for polyvinyl chloride. Such dialkyl pentaerythritol diphosphites are prepared according to U.S. Pat. No. 4,206,103 by the reaction of two moles of an alkyl alcohol with a diphenyl- or dichloropentaerythritol diphosphite, made by the reaction of two moles of triphenylphosphite or phosphorous trichloride with one mole of pentaerythritol. When diphenyl pentaerythritol diphosphite is the reactant, the spiro isomer comprises about half the combined total of spiro and caged isomers in the product. When dichloropentaerythritol diphosphite is substituted for the diphenyl pentaerythritol diphosphite, the product which results is the relatively pure spiro isomer, which is generally a solid.

The preparation of dialkylpentaerythritol diphosphites which are not contaminated by the presence of phenol is disclosed in U.S. Pat. No. 4,290,976. The process disclosed utilizes the dichloropentaerythritol diphosphite made from phosphorous trichloride and pentaerythritol as a starting material since it does not contain a phenyl group and there is no possibility of phenol being formed as a contaminant. The products of the process described are characterized by higher set points and as a result do not form stable one-phase mixtures with liquid mixed metal stabilizers.

U.S. Pat. No. 3,047,608 describes the preparation of trialkyl phosphites and dialkyl pentaerythritol diphosphites by transesterification from triphenyl phosphite using a dialkyl or diphenyl phosphite as catalyst. The completeness of the transesterification and the removal of the byproduct phenol is controlled by the addition of an excess of the higher aliphatic alcohol, and removal of that excess along with the residual phenol by slow co-distillation under vacuum. The use of the diphenyl phosphites as catalysts, however, is not efficient, and the product from reaction of pentaerythritol with two moles of triphenyl phosphite and four moles of the higher aliphatic alcohol is mostly in the spiro form, and is incompatible with liquid mixed metal stabilizers.

U.S. Pat. No. 6,362,260 describes liquid organic phosphites of low volatility, based on pentaerythritol, alkyl alcohols and alkyl phenols, which are essentially phenol-free, but which require a pentaerythritol core structure.

Accordingly, there remains a need for essentially phenol free phosphites (as used in this application to mean less than or equal to 0.5%) which have good compatibility, performance, low volatility, package stability with mixed metal stabilizers and good performance, eliminating the drawbacks typically associated with current state-of-the-art phenol-based phopshites such as didecyl phenyl phosphite or diphenyl decyl phosphite.

SUMMARY OF INVENTION

One aspect of the present invention is a phosphite useful as a thermal stabilizer in vinyl polymers, especially polyvinyl chloride resin, of very low or nil phenol content (less than 0.5%) which is compatible with liquid mixed metal stabilizers.

It is another aspect of the present invention to provide essentially phenol-free phosphites for use in PVC as an alternative to the conventional phenol-containing products such as phenyl diisodecyl phosphite and diphenyl isodecyl phosphite. It is easily recognized that phenol with a boiling point of 182° C., will be liberated significantly more quickly than either nonylphenol with a boiling point of 295° C. or para-cumylphenol with a boiling point of 335° C. both nonylphenol and para-cumyl phenol are insoluble in water, whereas phenol is moderately soluble.

It is a further aspect of the present invention to provide phosphite which use para-cumyl phenol in order to provide an essentially phenol-free derivative of the above mentioned conventional phosphites, yet provide equivalent or better performance to more traditional phosphite stabilizers used presently.

These and other objects of this invention will be evident when viewed in light of the drawings, detailed description and the pending claims.

BRIEF DESCRIPTION OF DRAWINGS

The invention may take physical form in certain parts and arrangements of parts, a preferred embodiment of which will be described in detail in the specification and illustrated in the accompanying drawings which form a part hereof, and wherein.

DETAILED DESCRIPTION

Figure 1:
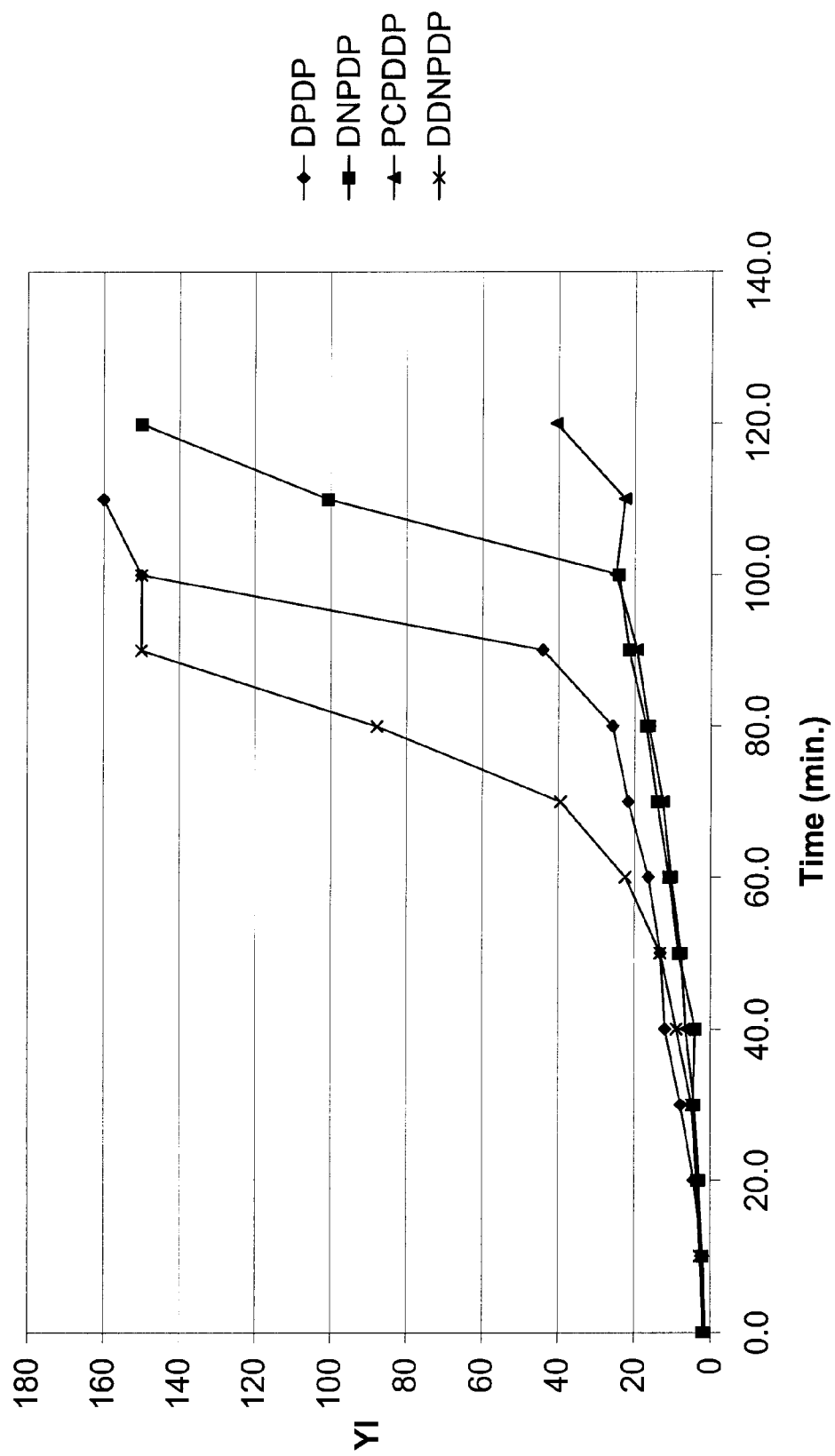
FIG. 1 is a graph of Yellowness Index over time (minutes) for various PVC compounds stabilized using various phosphites using the composition of Table III and the data of Table IV.

Various phenol-free phosphites for use in PVC as an alternative to the conventional phenol-containing products phenyl diisodecyl phosphite and diphenyl isodecyl phosphite were tested. The bulk of these phosphites utilize either nonylphenol or para-cumyl phenol in order to provide a phenol free derivative of the above mentioned conventional phosphites.

All phosphites were rated based on the stability performance they provide for PVC when used in the presence of a zinc compound. Testing parameters were thermal stability at 185° C. and 70° C., and weathering performance in a QUV weatherometer at 65° C.

The below listed phosphites were synthesized from triphenyl phosphite (TPP), alcohol, and the indicated functionality to produce a "phenol-free" phosphite. In this application, the following abbreviations will be employed:

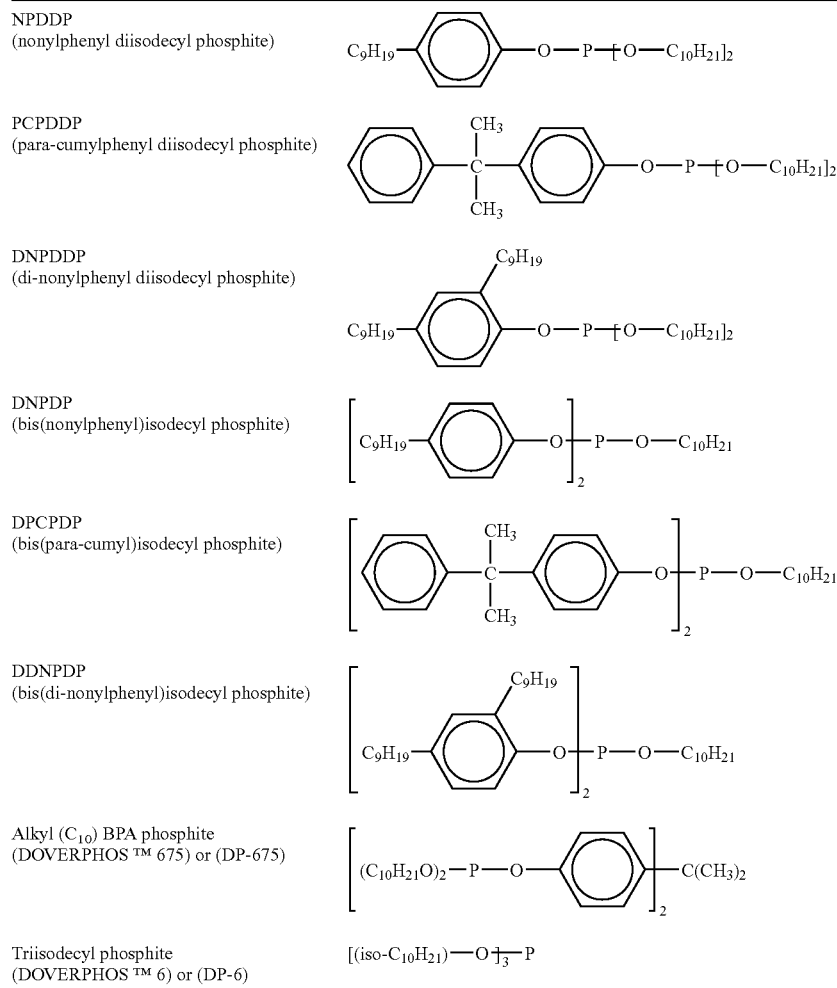

All compounds listed above were compared to the following phenol-containing phosphites for performance.

DPDP (or DoverPhos ™ 8) (diphenyl decyl phosphite) (DP-8)

PDDP (or DoverPhos ™ 7) (phenyl didecyl phosphite) (DP-7)

Tables I and II compare the volatilities of the various phosphites.

TABLE I

| Phosphite | T° C. for 10% Wt. reduction | T° C. for 24% Wt. reduction |
|---|---|---|
| DP-8 | 232 | 259 |
| DP-7 | 242 | 269 |
| DPCPDP | 276 | 322 |
| PCPDDP | 259 | 300 |

TABLE I-continued

| Phosphite | T° C. for 10% Wt. reduction | T° C. for 24% Wt. reduction |
|---|---|---|
| DNPDP | 279 | 318 |
| DP-675 | 222 | 267 |

Table I shows that phosphites based on para-cumyl phenol, rather than phenol, require much higher temperatures for 10% and 25% weight loss than the corresponding phosphites based on phenol. Compare for example DPDP (Doverphos™8) to its para-cumyl phenol analog DPCPDP.

DPDP

-continued

DPCPDP

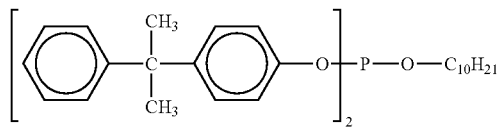

A temperature of 232° C. vs. 276° C. for 10% weight loss and 259° C. vs. 322° C. for a 25% weight loss. Also compare PDDP (Doverphos 7) to its para-cumyl phenol analog PCP-DDP.

PDDP

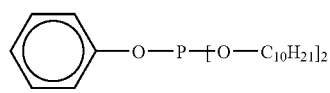

PCPDDP

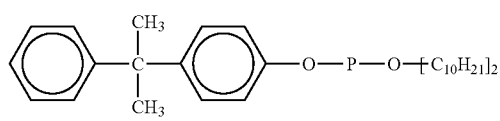

A temperature of 242° C. vs. 259° C. for 10% weight loss and 269° C. vs. 300° C. for a 25% weight loss. Lower volatility will result in less undesirable "fogging." Table II shows isothermal volatility at 185° C. (typical processing temperature) after 15 and 30 minutes.

TABLE II

| Phosphite | (% weight loss at 185° C.) | |
|---|---|---|
|  | After 15 min. | After 30 min. |
| DP-8 | 1.20 | 1.61 |
| DP-7 | 1.23 | 1.55 |
| DPCPDP | 0.78 | 1.07 |
| PCPDDP | 0.84 | 1.22 |

TABLE II-continued

| Phosphite | (% weight loss at 185° C.) | |
|---|---|---|
|  | After 15 min. | After 30 min. |
| DNPDP | 1.00 | 1.60 |
| DP-675 | 1.07 | 1.60 |

Comparing the same two sets of phosphites as before, at the end of 15 minutes at 185° C. DPDP (Doverphos 8) had a weight loss of 1.2% vs. 0.78% for DPCPDP, a value which is 53% less than that of DP-8. After 30 minutes at 185° C., DP-8 had a weight loss of 1.61 vs. 1.07 for DPCPDP, a value which is 50% less than DP-8. For DP-7 and its para-cumyl phenol analog PCPDDP, after 15 minutes, the weight loss was 1.23% in comparison of 0.84%, a value which is 46% less. After 30 minutes at that same temperature, the weight loss for DP-7 was 1.55% vs. 1.22%, a value which is 22% less.

The use of the above identified phosphites to serve as essentially phenol-free alternatives in zinc based stabilizer packages was studied using the chemical formulation listed below in Table III.

TABLE III

| Parts | Component |
|---|---|
| 100 | PVC Resin |
| 38 | DOP |
| 2.0 | ESO (epoxidized soybean oil) |
| 0.15 | Zinc stearate |
| 3.0 | phosphite |

All samples were compounded on a 2-roll mill at approximately 180° C. for 5 minutes. Compounded samples were tested for Mathis oven thermal stability at 185° C. for a 2 hour period.

Derivative phosphites of DoverPhos™8 (DP-8) performed exceptionally well in thermal stability evaluations. FIG. 1 shows yellowness index values, a measure of color stability, over time exposed to 185° C. based on the data in TABLE IV and the compositions of TABLE III.

TABLE IV

| Time (min.) | 0 | 10 | 20 | 30 | 40 | 50 | 60 | 70 | 80 | 90 | 100 | 110 | 120 |
|---|---|---|---|---|---|---|---|---|---|---|---|---|---|
| Additive |  |  |  |  |  | Yellowness Index |  |  |  |  |  |  |  |
| DPDP | 1.4 | 1.9 | 4.3 | 7.8 | 11.9 | 13.1 | 16.3 | 21.6 | 25.7 | 44.1 | 150 | 160 |  |

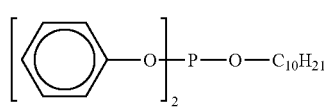

| DNPDP | 2 | 2 | 3 | 4.5 | 4 |  | 8.4 | 10.9 | 14 | 16.9 | 21.4 | 24.1 | 100.7 | 150 |

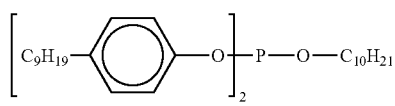

TABLE IV-continued

| Time (min.) Additive | 0 | 10 | 20 | 30 | 40 | 50 | 60 | 70 | 80 | 90 | 100 | 110 | 120 |
|---|---|---|---|---|---|---|---|---|---|---|---|---|---|
| | | | | | | Yellowness Index | | | | | | | |
| DPCPDP | 1.6 | 2.3 | 2.9 | 4.2 | 6.5 | 7.7 | 10.3 | 12.5 | 16.2 | 19.3 | 24.8 | 22.5 | 40.5 |

$$\left[ \text{Ph-C(CH}_3\text{)}_2\text{-C}_6\text{H}_4\text{-O} \right]_2 \text{P-O-C}_{10}\text{H}_{21}$$

| DDNPDP | 1.7 | 2.7 | 3.5 | 4.9 | 8.9 | 13.2 | 22.4 | 39.4 | 87.7 | 150 | 150 | | |

$$\left[ (C_9H_{19})_2C_6H_3\text{-O} \right]_2 \text{P-O-C}_{10}\text{H}_{21}$$

The data above indicates both the para-cumylphenyl derivative (DPCPDP) and bis nonylphenyl isodecyl phosphite (DNPDP) derivatives offer improved performance compared to diphenyl isodecyl phosphite (DPDP). However, the performance of bis (dinonylphenyl)isodecyl phosphite (DDNPDP) did not perform as well although it did show that phenol-free derivatives can offer similar performance. The DoverPhos™ 7 based derivatives (PDDP) also exhibited the comparable trends of improved performance in PVC systems.

Figure 2:
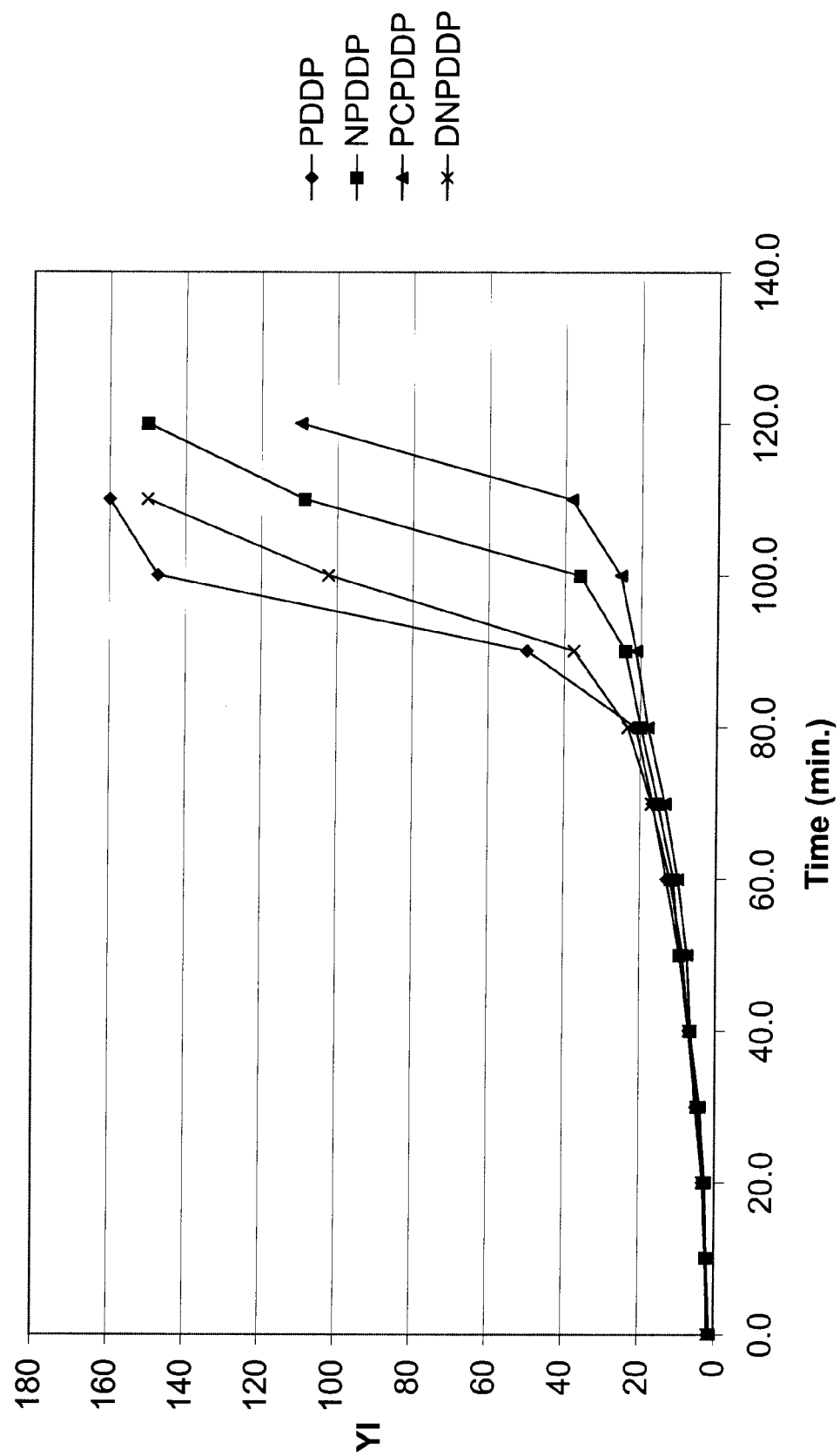
FIG. 2 is a graph of Yellowness Index over time (minutes) for various PVC compounds stabilized using various phosphites using the composition of Table III and the data of Table V.

The paracumyl phenol version of the phenyl diisodecyl phosphite (PCPDDP) and the nonylphenyl version (NPDDP) both performed exceptionally well (especially PCPDDP), while the dinonylphenyl derivative offers equivalent performance to the DoverPhos™7 phosphite (PDDP) as illustrated in FIG. 2, which shows yellowness index values over time exposed to 185° C. based on the data in TABLE V and the compositions of TABLE III. As used in the table, the following abbreviations have the identified chemical formulas.

TABLE V

| Time (min.) Additive | 0 | 10 | 20 | 30 | 40 | 50 | 60 | 70 | 80 | 90 | 100 | 110 | 120 |
|---|---|---|---|---|---|---|---|---|---|---|---|---|---|
| | | | | | | Yellowness Index | | | | | | | |
| PDDP | 1.7 | 2.2 | 3.2 | 5.1 | 7 | 9.4 | 13 | 16.6 | 21.1 | 49.8 | 147.2 | 160 | |

$$\text{Ph-O-P}[\text{O-C}_{10}\text{H}_{21}]_2$$

| NPDDP | 1.3 | 2.2 | 2.9 | 4.7 | 6.4 | 9.5 | 11.1 | 15.2 | 19.8 | 24 | 36 | 108.6 | 150 |

$$C_9H_{19}\text{-C}_6H_4\text{-O-P}[\text{O-C}_{10}\text{H}_{21}]_2$$

| PCPDDP | 1.2 | 2 | 2.5 | 4 | 6.5 | 7.4 | 9.9 | 13.4 | 17.9 | 21.2 | 25.3 | 38.3 | 109.6 |

$$\text{Ph-C(CH}_3\text{)}_2\text{-C}_6H_4\text{-O-P}[\text{O-C}_{10}\text{H}_{21}]_2$$

| DNPDDP | 1.8 | 2 | 3.2 | 4.9 | 6.9 | 8.6 | 12 | 16.9 | 23.2 | 37.5 | 102.2 | 150 | |

$$(C_9H_{19})_2C_6H_3\text{-O-P}[\text{O-C}_{10}H_{21}]_2$$

Figure 3:
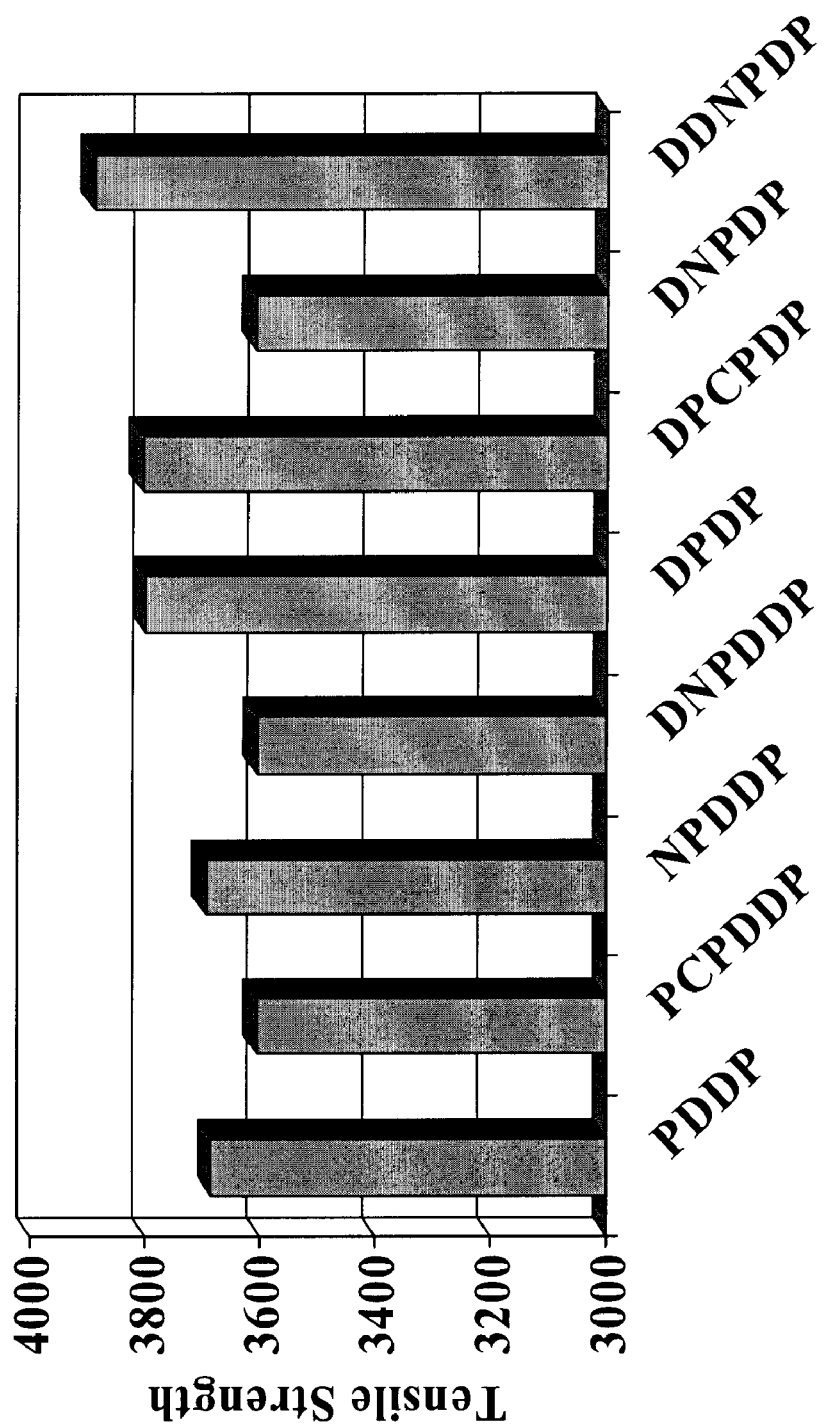
FIG. 3 is a graph of tensile strength (psi) of various phosphites in PVC resin using the composition of Table III.

The tensile strength (in psi) of the resultant molded PVC compounds all appeared to be relatively equivalent showing no significant changes in the overall mechanical properties, as would be expected and as illustrated in FIG. 3 for the compositions of TABLE III.

Figure 4:
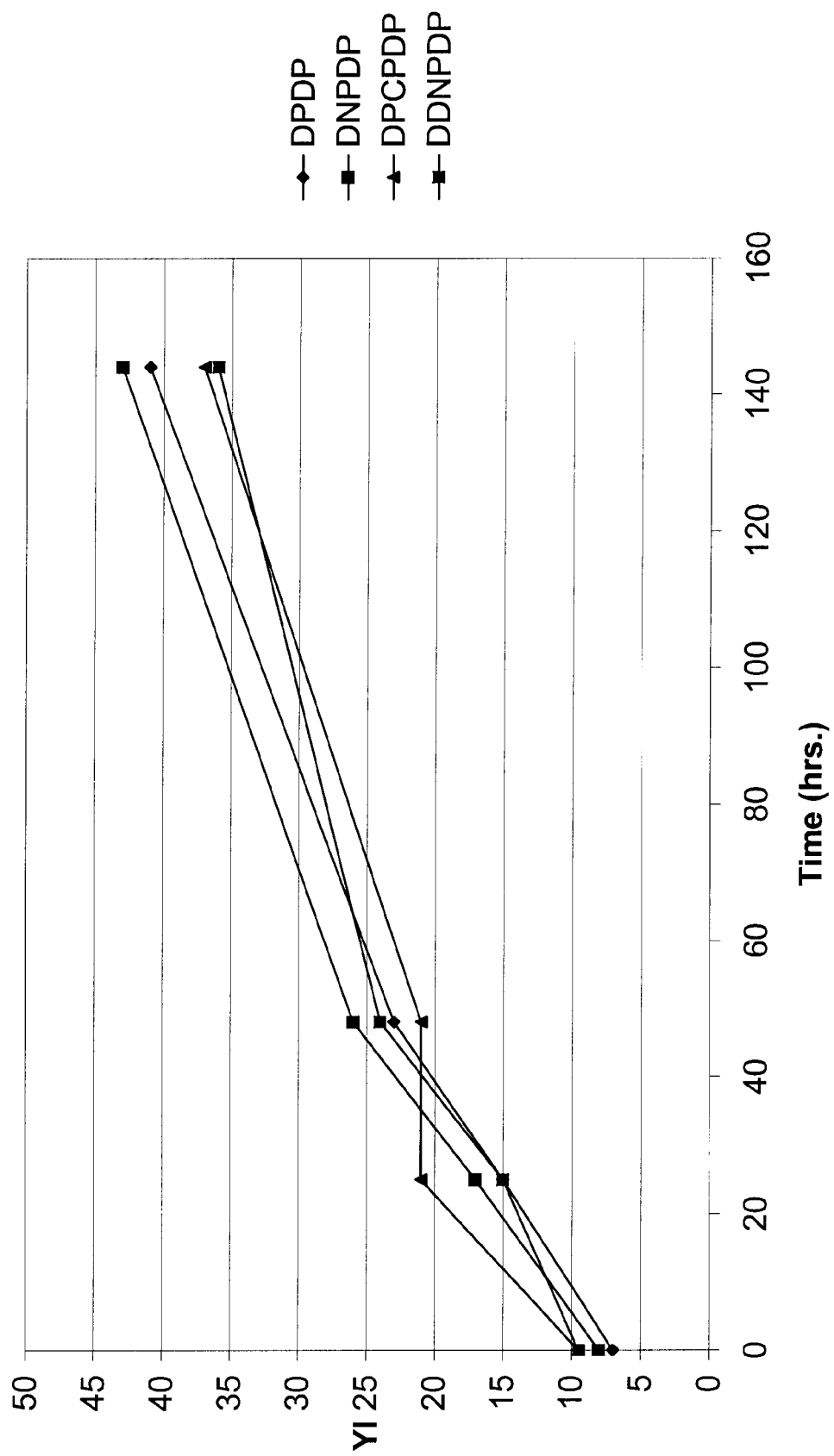
FIG. 4 is a graph of Yellowness Index color stability for various phosphites in PVC resin using the composition of Table VI vs. exposure time (hours) in a QUV Weatherometer.
Figure 5:
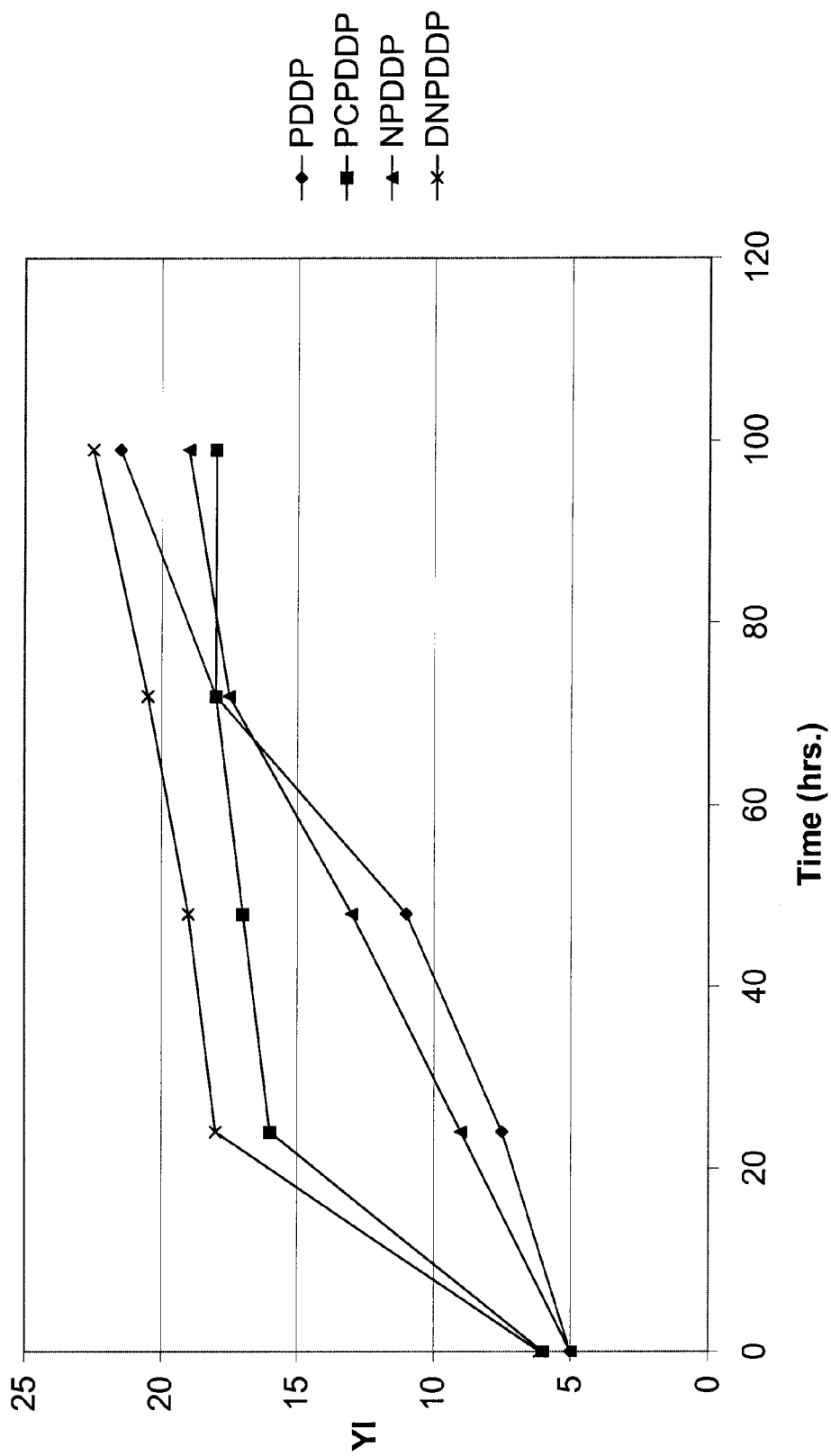
FIG. 5 is a graph of Yellowness Index over time (minutes) for various phosphites in PVC resin using the composition of Table VI vs. exposure time (hours) in a QUV Weatherometer.

QUV analysis at 65° C. shows relatively equivalent performance for a filled PVC formulation as shown in FIGS. 4-5 using the composition of TABLE VI.

TABLE VI

| Parts | Component |
|---|---|
| 100 | PVC Resin |
| 40 | DOP |
| 5.0 | ESO (epoxidized soybean oil) |
| 0.3 | Zinc stearate |
| 25 | $CaCO_3$ |
| 2.5 | phosphite |

This applies to both the DoverPhos™7 and DoverPhos™ 8 based derivatives. The exception in QUV performance appears to be di-nonylphenol diisodecyl phoshite, which did show some increased initial discoloration.

Additional work was then done on examining possible variations of a phenol free phosphite. In particular we examined the paracumylphenyl diisodecyl phosphite. Two more products were made to evaluate in zinc based stabilizer systems, namely ethoxy-paracumylphenyl diisodecyl phosphite (EPCPDDP) and propoxy-paracumylphenyl diisodecyl phosphite (PPCPDDP) wherein m=2 and 3 respectively, but can be any integral value from 1 to 4.

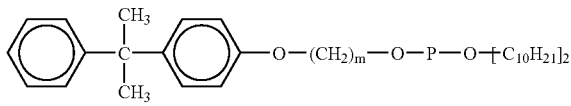

Figure 6:
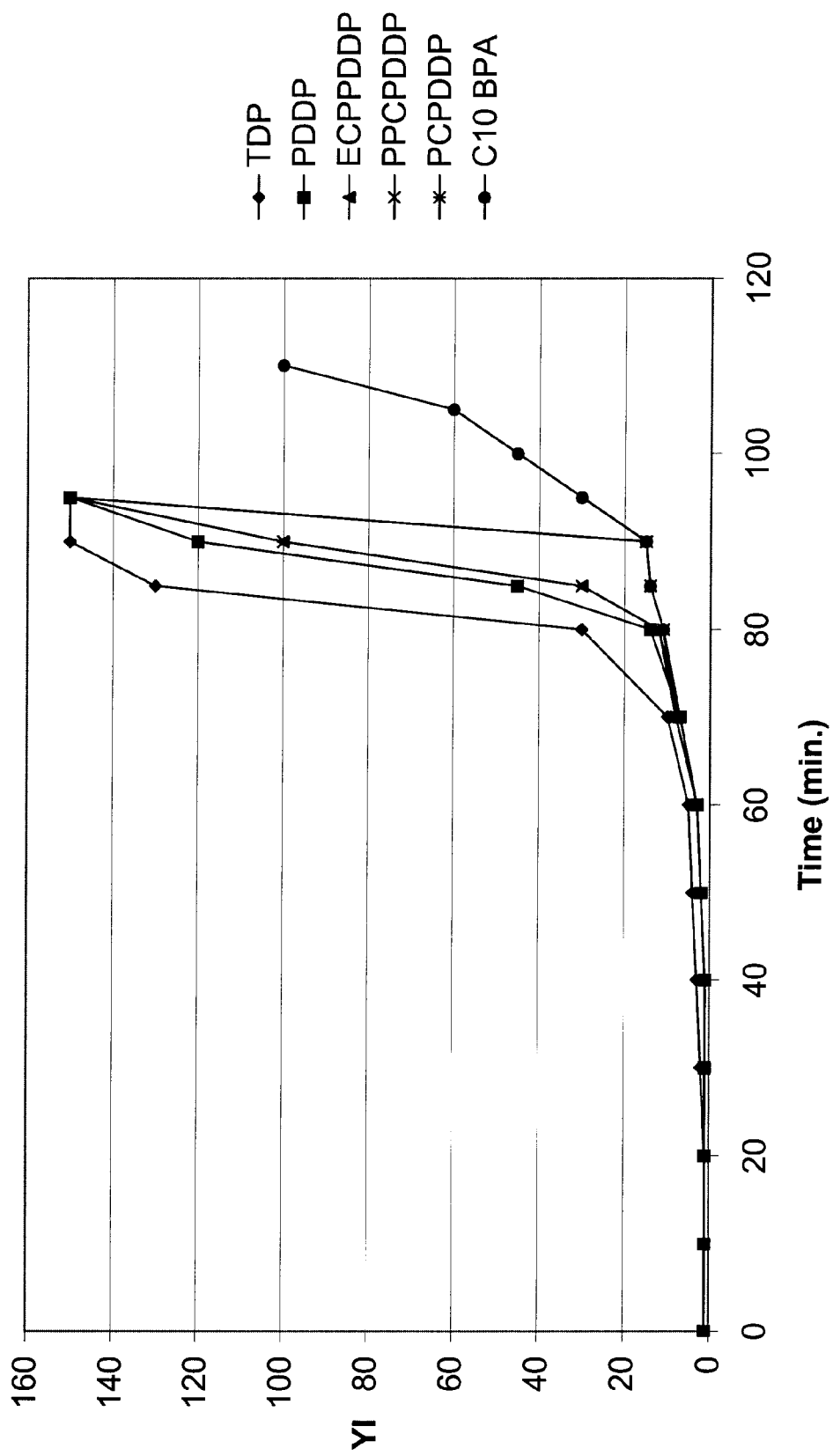
FIG. 6 is a graph of Yellowness Index over time (minutes) for various phosphites comparing the Color Stability measured by the Yellowness Index (YI) at 185° C. using the composition of Table III.
Figure 7:
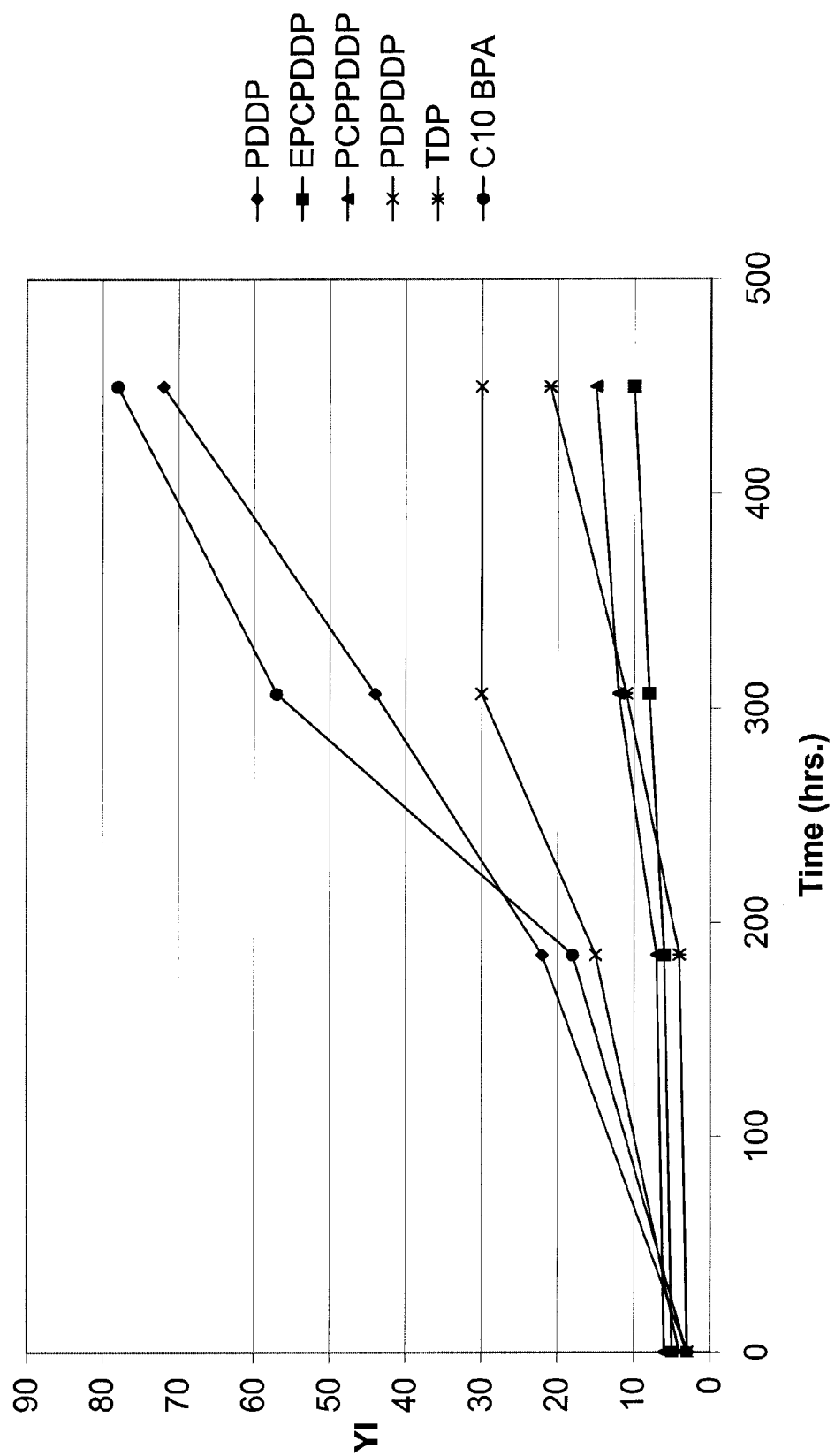
FIG. 7 is a graph of Yellowness Index Yellowness Index over time (hours) for various phosphites in PVC resin using the composition of Table VI vs. exposure time (hours) in Xenon arc weathering performance at 65° C. using the composition of Table III.

The performances of these two phosphites were compared to various other phosphites, as well as the PCPDDP product. Thermal stabilities for these phosphites closely matched the PCPDDP phosphite which, offered slightly improved long term stability compared to the PDDP product. This performance was a little worse than the typical DoverPhos™ 675 ($C_{10}$ bisphenol-A phosphite) but significantly better in long term performance than the DoverPhos™ 6 phosphite (triisodecyl phosphite) as illustrated in FIG. 6. Xenon arc weathering performance at 65° C. showed exceptional performance from the ethoxylated and propoxylated PCP derivative phosphites as shown in FIG. 7 PCPDDP peforms well versus the DoverPhos™ 7 phosphite however, only the ethoxy and propoxy versions of this phosphite offer better weathering performance than tridecyl phosphite (TDP) As used above, the following chemical formulas are associated with the following abbreviations.

In more generic form, what has been illustrated is an essentially phenol-free forming phosphite additive having the following Markush formulation:

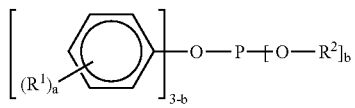

wherein
$R^1$ is selected from the group consisting of

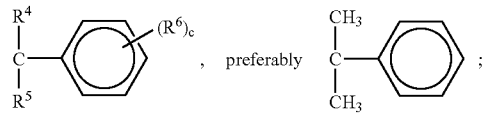

$R^2$ is selected from the group consisting of $C_{8-16}$ alkyls; (preferably $C_{10}H_{21}$)
a is an integral value ranging from 1 to 4 inclusive;
b is an integral value ranging from 1 to 2 inclusive;
$R^4$ and $R^5$ are independently selected from the group consisting of $C_{1-3}$ alkyls;
$R^6$ is selected from the group consisting of $C_{8-12}$ alkyls and $C_{8-12}$ alkoxy compounds; and
c is an integral value ranging from 0 to 4 inclusive.

In an alternative generic form, what has been illustrated is an essentially phenol-free forming phosphite additive having the following Markush formulation

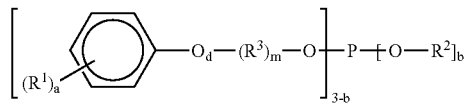

wherein
$R^1$ is selected from the group consisting of

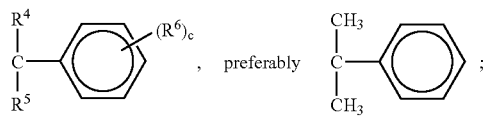

$R^2$ is selected from the group consisting of $C_{8-16}$ alkyls; (preferably $C_{10}H_{21}$)
$R^3$ Is selected from the group consisting of $C_{1-4}$ alkyls alkylenes, (preferably ethylene and propylene)
m Is an integral value ranging from 0 to 1 inclusive;
a is an integral value ranging from 1 to 4 inclusive;
b is an integral value ranging from 1 to 2 inclusive;
$R^4$ and $R^5$ are independently selected from the group consisting of $C_{1-3}$ alkyls;
$R^6$ Is selected from the group consisting of $C_{8-12}$ alkyls and $C_{8-12}$ alkoxy compounds;
c is an integral value ranging from 0 to 4 inclusive; and
d is equal to m.

While halogenated polymer resins, particularly PVC are believed to be one of the preferred embodiments of this invention, the teachings and claims are not so limited. In fact, the compositions and the methods of the current invention may be used to stabilize any of the polymers known in the art, such as polyolefins, polyesters, polyurethanes, polyalkylene terephthalates, polysulfones, polyimides, polyphenylene ethers, styrenic polymers, polycarbonates, acrylic polymers, polyamides, polyacetals, halide containing polymers and polyolefin homopolymers and copolymers. Additionally included would be mixtures of different polymers, such as polyphenylene ether/styrenic resin blends, polyvinylchloride/ABS or other impact modified polymers, such as methacrylonitrile containing ABS, and polyester/ABS or polyester plus some other impact modifier may also be used. Such polymers are available commercially or may be made by means well known in the art. However, the diphosphites of the invention are particularly useful in thermoplastic polymers, such as polyolefins, polycarbonates, polyesters, polyphenylene ethers thermoplastic polymers, such as polyolefins, polycarbonates, polyesters, polyphenylene ethers and styrenic polymers, due to the extreme temperatures at which the thermoplastic polymers are often processed and/or used.

Polymers of monoolefins and diolefins, for example would include polypropylene, polyisobutylene, polybutene-1, polymethylpentene-1, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE) and linear low density polyethylene (LLDPE) may be used. Mixtures of these polymers, for example mixtures of polypropylene with polyisobutylene, polypropylene with polyethylene (for example PP/HDPE), may also be used. Also useful are copolymers of monoolefins and diolefins with each other or with other vinyl monomers, such as, for example, ethylene/propylene, LLDPE and its mixtures with LDPE, propylene/butene-1, ethylene/hexene, ethylene/ethyl pentene, ethylene/heptene, ethylene/octene, propylene/butadiene, isobutylene/isoprene, ethylene/alkyl acrylates, ethylene/alkyl methacrylates, ethylene/vinyl acetate (EVA) or ethylene/acrylic acid copolymers (EAA) and their salts (ionomers) and terpolymers of ethylene with propylene and a diene, such as hexadiene, dicyclopentadiene or ethylidene-norbornene; as well as mixtures of such copolymers and their mixtures with polymers mentioned above, for example polypropylene/ethylene-propylene copolymers, LDPE/EVA, LDPE/EAA, LLDPE/EVA and LLDPE/EAA.

Thermoplastic polymers may also include styrenic polymers, such as polystyrene, poly-(p-methylstyrene), poly-(α-methylstyrene), copolymers of styrene, p-methylstyrene or alpha-methylstyrene with dienes or acrylic derivatives, such as, for example, styrene/butadiene, styrene/acrylonitrile, styrene/alkyl methacrylate, styrene/maleic anhydride, styrene/butadiene/ethyl acrylate, styrene/acrylonitrile/methacrylate; mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/styrene, styrene/isoprene/styrene, styrene/ethylene/butylene/styrene or styrene/ethylene/propylene/styrene. Styrenic polymers may additionally or alternatively include graft copolymers of styrene or alpha-methylstyrene such as, for example, styrene on polybutadiene, styrene on polybutadiene-styrene or polybutadiene-acrylonitrile; styrene and acrylonitrile (or methacrylonitrile) on polybutadiene; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures of the styrenic copolymers indicated above.

Nitrile polymers are also useful. These include homopolymers and copolymers of acrylonitrile and its analogs such as methacrylonitrile, such as polyacrylonitrile, acrylonitrile/butadiene polymers, acrylonitrile/alkyl acrylate polymers, acrylonitrile/alkyl methacrylate/butadiene polymers, acrylonitrile/butadiene/styrene (ABS), and ABS which includes methacrylonitrile.

Polymers based on acrylic acids, such as acrylic acid, methacrylic acid, methyl methacrylate acid and ethacrylic acid and esters thereof may also be used. Such polymers include polymethylmethacrylate, and ABS-type graft copolymers wherein all or part of the acrylonitrile-type monomer has been replaced by an acrylic acid ester or an acrylic acid amide. Polymers including other acrylic-type monomers, such as acrolein, methacrolein, acrylamide and methacrylamide may also be used.

Halogen-containing polymers are particularly preferred. These include resins such as polychloroprene, epichlorohydrin homopolymers and copolymers, polyvinyl chloride, polyvinyl bromide, polyvinyl fluoride, polyvinylidene chloride, chlorinated polyethylene, chlorinated polypropylene, fluorinated polyvinylidene, brominated polyethylene, chlorinated rubber, vinyl chloride-vinylacetate copolymer, vinyl chloride-ethylene copolymer, vinyl chloride propylene copolymer, vinyl chloride-styrene copolymer, vinyl chloride-isobutylene copolymer, vinyl chloride-vinylidene chloride copolymer, vinyl chloride-styrene-maleic anhydride tercopolymer, vinyl chloride-styrene-acrylonitrile copolymer, vinyl chloride-isoprene copolymer, vinyl chloride-chlorinated propylene copolymer, vinyl chloride-vinylidene chloride-vinyl acetate tercopolymer, vinyl chloride-acrylic acid ester copolymers, vinyl chloride-maleic acid ester copolymers, vinyl chloride-methacrylic acid ester copolymers, vinyl chloride-acrylonitrile copolymer and internally plasticized polyvinyl chloride.

Other useful thermoplastic polymers include homopolymers and copolymers of cyclic ethers, such as polyalkylene glycols, polyethylene oxide, polypropylene oxide or copolymers thereof with bis-glycidyl ethers; polyacetals, such as polyoxymethylene and those polyoxymethylene which contain ethylene oxide as a comonomer; polyacetals modified with thermoplastic polyurethanes, acrylates or methacrylonitrile containing ABS; polyphenylene oxides and sulfides, and mixtures of polyphenylene oxides with polystyrene or polyamides; polycarbonates and polyester-carbonates; polysulfones, polyethersulfones and polyetherketones; and polyesters which are derived from dicarboxylic acid and diols and/or from hydroxycarboxylic acids or the corresponding lactones, such as polyethylene terephthalate, polybutylene terephthalate, poly-1,4-dimethyliol-cyclohexane terephthalate, poly-[2,2,4-(4-hydroxyphenyl)-propane] terephthalate and polyhydroxybenzoates as well as block copolyetheresters derived from polyethers having hydroxyl end groups.

Polyamides and copolyamides which are derived from diamines and dicarboxylic acids and/or from aminocarboxylic acids or the corresponding lactams, such as polyamide-4, polyamide-6, polyamide-6/6, polyamide-6/10, polyamide-6/9, polyamide-6/12, polyamide-4/6, polyamide-11, polyamide-12, aromatic polyamides obtained by condensation of m-xylene, diamine and adipic acid; polyamides prepared from hexamethylene diamine and isophthalic and/or terephthalic acid and optionally an elastomer as modifier, for example, poly-2,4,4-trimethylhexamethylene terephthalamide or poly-m-phenylene isophthalamide may be useful. Further copolymers of the aforementioned polyamides with polyolefins, olefin copolymers, ionomers or chemically bonded or grafted elastomers; or with polyethers, such as for instance, with polyethylene glycol, polypropylene glycol or polytetramethylene glycols, and polyamides or copolyamides modified with EPDM or ABS may be used.

The resulting stabilized polymer compositions comprising the phosphites made by the process of this invention may optionally also contain various conventional additives, such as the following:

(1) Antioxidants (1.1) Alkylated monophenols, for example
2,6-di-tert-butyl-4-methylphenol,
2-tert-butyl-4,6-dimethylphenol,
2,6-di-tert-butyl-4-ethylphenol,
2,6-di-tert-butyl-4-n-butylphenol,
2,6-di-tert-butyl-isobutylphenol,
2,6-di-cyclopentyl-4-methylphenol,
2-α-methylcyclohexyl)-4,6-di methyl phenol,
2,6-dioctadecyl-4-methylphenol,
2,4,6-tricyclohexylphenol,
2,6-di-tert-butyl-4-methoxymethylphenol and
2,6-di-nonyl-4-methylphenol.

(1.2) Alkylated hydroquinones, for example
2,6-di-tert-butyl-4-methoxyphenol,
2,5-di-tert-butylhydroquinone,
2,5-di-tert-amylhydroquinone and
2,6-diphenyl-4-octadecyloxyphenol.

(1.3) Hydroxylated thiodiphenyl ethers, for example
2,2'-thiobis-(6-tert-butyl-4-methyl phenol),
2,2'-thiobis-(4-octyl phenol),
4,4'-thiobis-(6-tert-butyl-3-methyl phenol),
4,4'-thiobis-(6-tert-butyl-2-methyl phenol).

(1.4) Alkylidene bislphenols, for example
2,2'-methylenebis-(6-tert-butyl-4-methyl phenol),
2,2'-methylenebis-(6-tert-butyl-4-ethylphenol),
2,2'-methylenebis-[4-methyl-6-α-methylcyclohexyl) -phenol], 2,2'-methylenebis-(4-methyl-6-cyclohexylphenol),
2,2'-methylenebis-(6-nonyl-4-methylphenol),
2,2'-methylenebis-(4,6-di-tert-butylphenol),
2,2'-ethylidenebis-(4,6-di-tert-butylphenol),
2,2'-ethylidenebis-(6-tert-butyl-4-isobutylphenol),
2,2'-methylenebis-[6-(α-methylbenzyl)-4-nonylphenol],
2,2'-methylenebis-[6-(α,α-dimethylbenzyl)-4-nonylphenol], 4,4'-methylenebis-(2,6-di-tert-butylphenol),
4,4'-methylenebis-(6-tert-butyl-2-methyl phenol),
1,1-bis-(5-tert-butyl-4-hydroxy-2-methylphenyl)-butane,
2,6-bi s-(3-tert-butyl-5-methyl-2-hydroxybenzyl)-4-methylphenol,
1,1,3-tris-(5-tert-butyl-4-hydroxy-2-methylphenyl)-butane,
1,1-bis-(5-tert-butyl-4-hydroxy-2-methylphenyl)-3-n-dodecylmercaptobutane, ethylene glycol bis-[3,3-bis-(3'-tert-butyl-4'-hydroxyphenyl)-butyrate], bis-(3-tert-butyl-4-hydroxy-5-methyl phenyl)-dicyclopentadiene and bis-[2-(3'-tert-butyl-2'-hydroxy-5'-methylbenzyl)-6-tert-butyl-4-methylphenyl]terephthalate.

(1.5) Benzyl compounds, for example
1,3,5-tris-(3,5-di-tert-butyl-4-hydroxybenzyl)-2,4,6-trimethylbenzene, bis-(3,5-di-tert-butyl-4-hydroxybenzyl)sulfide, isooctyl 3,5-di-tert-butyl-4-hydroxybenzylmercaptoacetate, bis(4-tert-butyl-5-hydroxy-2,6-methylbenzyl)-dithiolterephthalate,
1,3,5-tris-(3,5-di-tert-butyl-4-hydroxybenzyl)isocyanurate,
1,3,5-tris-(4-tert-butyl-3-hydroxy-2,6-dimethylbenzyl) isocyanurate, dioctadecyl
3,5-di-tert-butyl-4-hydroxybenzylphosphonate, the Ca salt of monoethyl
3,5-di-tert-butyl-4-hydroxybenzylphosphonate and 1,3,5-tris-(3,5-dicyclohexyl-4-hydroxybenzyl)isocyanurate.

(1.6) Acylaminophenols, for example
4-hydroxylauranilide, 4-hydroxystearanilide,
2,4-bis-(octylmercapto)-6-(3,5-di-tert-butyl-4-hydroxyaniline-s-triazine and octyl N-(3,5-di-tert-butyl-4-hydroxyphenyl)-carbamate.

(1.7) Esters of β-(3,5-di-tert-butyl-4-hydroxyphenyl)-propionic acid, with monohydric or polyhydric alcohols, for example methanol, octadecanol, 1,6-hexanediol, neopentyl glycol, thiodiethylene glycol, diethylene glycol, triethylene glycol, pentaerythritol, tris-(hydroxyethyl)isocyanurate and N,N'-bis-(hydroxyethyl)oxamide.

(1.8) Esters of β-(5-tert-butyl-4-hydroxy-3-methylphenyl)-propionic acid with monohydric or polyhydric alcohols, for example methanol, octadecanol, 1,6-hexanediol, neopentyl glycol, thiodiethylene glycol, diethylene glycol, triethylene glycol, pentaerythritol, tris-(hydroxyethyl)isocyanurate and N,N'-bis-(hydroxyethyl)oxamide.

(1.9) Esters of β-(3,5-dicyclohexyl-4-hydroxyphenyl)-propionic acid with monohydric or polyhydric alcohols, for example methanol, octadecanol, 1,6-hexanediol, neopentyl glycol, thiodiethylene glycol, diethylene glycol, triethylene glycol, pentaerythritol, tris-(hydroxyethyl)isocyanurate and N,N'-bis-(hydroxyethyl)oxamide.

(1.10) Amides of β-(3,5-di-tert-butyl-4-hydroxyphenyl)-propionic acid, for example
N,N'-bis-(3,5-di-tert-butyl-4-hydroxyphenyl-propionyl) -hexamethylenediamine,
N,N'-bis-(3,5-di-tert-butyl-4-hydroxyphenylpropionyl) -trimethylenediamine and
N,N'-bis-(3,5-di-tert-butyl-4-hydroxyphenylpropionyl) -hydrazine.

(2) UV Absorbers and Light Stabilizers.

(2.1) 2-(2'-hydroxyphenyl)-benzotriazoles, for example the 5'-methyl-, 3',5'-di-tert-butyl-, 5'-tert-butyl-,
5'-(1,1,3,3-tetramethylbutyl)-,
5-chloro-3',5'-di-tert-butyl-,
5-chloro-3'-tert-butyl-5'-methyl-,
3'-sec-butyl-5'-tert-butyl-, 4'-octoxy-,
3',5'-di-tert-amyl-, 3',5'-bis-(α,α-dimethylbenzyl)-derivatives.

(2.2) 2-Hydroxybenzophenones, for example the
4-hydroxy-, 4-methoxy-, 4-octoxy-, 4-decyloxy-,
4-dodecyloxy-, 4-benzyloxy-, 4,2',4'-trihydroxy- or 2'-hydroxy-4,4'-dimethoxy-derivatives.

(2.3) Esters of unsubstituted or substituted benzoic acids, for example 4-tert-butylphenyl salicylate, phenyl salicylate, octylphenyl salicylate, dibenzoylresorcinol, bis-(4-tert-butylbenzoyl)-resorcinol, benzoylresorcinol,
2,4-di-tert-butylphenyl
3,5-di-tert-butyl-4-hydroxybenzoate and hexadecyl
3,5-di-tert-butyl-4-hydroxybenzoate.

(2.4) Acrylates, for example ethyl or isooctyl α-(cyano-β, β-diphenylacrylate, methyl α-(carbomethoxycinnamate, methyl or butyl α-(cyano-β-methyl-p-methoxycinnamate, methyl α-(carbomethoxy-p-methoxycinnamate or N-(β-carbomethoxy-β-cyanovinyl)-2-methylindoline.

(2.5) Nickel compounds, for example nickel complexes of 2,2'-thiobis-[4-(1,1,3,3-tetramethylbutyl)-phenol], such as the 1:1 complex or the 1:2 complex, if appropriate with additional ligands, such as n-butylamine, triethanolamine or N-cyclohexyldiethanolamine, nickel dibutyldithiocarbamate, nickel salts of monoalkyl 4-hydroxy-3,5-di-tert-butylbenzylphosphonates, such as the methyl or ethyl ester, nickel complexes of ketoximes, such as 2-hydroxy-4-methylphenyl undecyl ketoxime, or nickel complexes of 1-phenyl-4-lauroyl-5-hydroxypyrazole, if appropriate with additional ligands.

(2.6) Oxamides, for example 4,4'-di-octyloxyoxanilide, 2,2'-di-octyloxy-5,5'-di-tert-butyloxanilide, 2,2'-di-dodecyloxy-5,5'-di-tert-butyloxanilide, 2-ethoxy-2'-ethyloxanilide, N,N'-bis-(3-dimethylaminopropyl)-oxalamide, 2-ethoxy-5-tert-butyl-2'-ethyloxanilide and a mixture thereof with
2-ethoxy-2'-ethyl-5,4'-di-tert-butyloxanilide or mixtures of o-methoxy- and p-methoxy-disubstituted oxanilides and of o-ethoxy- and p-ethoxy-disubstituted oxanilides.

(3) Metal deactivators, for example, N,N'-diphenyloxamide,
N-salicylal-N'-salicyloylhydrazine,
N,N'-bis-(salicyloyl)-hydrazine,
N,N'-bis-(3,5-di-tert-butyl-4-hydroxyphenylpropionyl) -hydrazine, 3-salicyloylamino-1,2,4-triazole and bis(benzylidene)-oxalic acid dihydrazide.

(4) Phosphites and phosphonites, for example triphenyl phosphite, diphenyl alkyl phosphites, phenyl dialkyl phosphites, tris-(nonylphenyl) phosphite, trilauryl phosphite, trioctadecyl phosphite, distearyl pentaerythritol diphosphite, tris-(2,4-di-tert-butylphenyl) phosphite, diisodecyl pentaerythritol diphosphite, bis-(2,4-di-tert-butylphenyl) pentaerythritol diphosphite, tristearyl sorbitol triphosphite, tetrakis-(2,4-di-tert-butylphenyl) 4,4'-biphenylene diphosphonite and
3,9-bis-(2,4-di-tert-butylphenoxy)-2,4,8,1-tetraoxa-3,9-diphosphaspiro[5.5]undecane.

(5) Peroxide scavengers, for example esters of β-thiodipropionic acid, for example the lauryl, stearyl, myristyl or tridecyl esters, mercaptobenzimidazole, the zinc salt of 2-mercaptobenzimidazole, zinc dibutyldithiocarbamate, dioctadecyl disulfide and pentaerythritol tetrakis-(β-dodecylmercapto) propionate.

(6) Polyamide stabilizers, for example copper salts in combination with iodides and/or phosphorus compounds and salts of divalent manganese.

(7) Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, barium stearate, magnesium stearate, sodium ricinoleate, potassium palmitate, antimony pyrocatecholate and zinc pyrocatecholate.

(8) Nucleating agents, for example, 4-t-butyl-benzoic acid, adipic acid, diphenylacetic acid.

(9) Fillers and reinforcing agents, for example, calcium carbonate, silicates, glass fibers, asbestos, talc, kaolin, mica, barium sulfate, metal oxides and hydroxides, carbon black, graphite.

(10) Aminoxypropanoate derivatives such as methyl-3-[N,N-dibenzylaminoxy]propanoate; ethyl-3-[N,N-dibenzylaminoxy]propanoate; 1,6-hexamethylene-bis[3-(N,N-dibenzylaminoxy)propanoate]; methyl-[2-(methyl)-3(N,N-dibenzylaminoxy)propanoate]; octadecyl-3-[N,N-dibenzylaminoxy]propanoic acid;
tetrakis[(N,N-dibenzylaminoxy)ethyl carbonyl oxymethyl] methane; octadecyl-3-[N,N-diethylaminoxy]propanoate; 3-[N,N-dibenzylaminoxy]propanoic acid potassium salt; and 1,6-hexamethylene bis[3-(N-allyl-N-dodecyl aminoxy) propanoate].

(11) Other additives, for example, plasticizers, lubricants, emulsifiers, pigments, optical brighteners, flame-proofing agents, anti-static agents, blowing agents and thiosynergists such as dilaurylthiodipropionate or distearylthiodipropionate.

Hindered phenolic antioxidants may also be present in the polymer composition. Use of bis(alkylpheny)l pentaerythritol diphosphites of the present invention may result in enhanced polymer protection by reducing the formation of color resulting from the presence of the phenols. Such phenolic antioxidants include in addition to those specifically mentioned previously, n-octadecyl-3,5-di-t-butyl-4-hydroxyhydrocinnamate, neopentaneterayl tetrakis-(3,5-di-t-butyl-4-hydroxyl-hydrocinnamate), din-octadecyl-3,5-di-t-butyl-4-hydroxybenzyl-phosphonate,
1,3,5-tris(3,5-di-t-butyl-4-hydroxybenzyl-)isocyanurate, thiodiethylene-bis(3,5-di-t-butyl-4-hydroxyhydrocinnamate),
1,3,5-trimethyl-2,4,6-tris(3,5-di-t-butyl-4-hydroxybenzyl) benzene, 3,6-di-oxaoctamethylene bis(3-methyl-5-t-butyl-4-hydroxyhydrocinnamate),
2,6-di-t-butyl-p-cresol, 2,2'-ethylidene-bis(4,6-di-t-butylphenol),
1,3,5-tris-(2,6-di-methyl-4-t-butyl-3-hydroxybenzyl)isocyanurate,
1,1,3-tris-(2-methyl-4-hydroxy-5-t-butylphenyl)butane,
1,3,5-tris[2-(3,5-di-t-butyl-4-hydroxyhydrocinnainoloxy)-ethyl]-isocyanurate,
3,5-di-(3,5-di-t-butyl-4-hydroxybenzyl)-mesitol, hexamethylene-bis(3,5-di-t-butyl-4-hydroxyhydrocimiamate),
1-(3,5-di-t-butyl-4-hydroxyanilino)-3,5-di(octylthio)-s-triazine,
N,N'-hexamethylene-bis(3,5-di-t-butyl-4-hydroxyhydrocinnamamide), calcium
bis(ethyl-3,5-di-t-butyl-4-hydroxybenzylphosphonate),
ethylene bis[3,3-di(3-t-butyl-4-hydroxyphenyl)butyrate], octyl
3,5-di-t-butyl-4-hydroxybenzylmercaptoacetate, bis(3,5-di-t-butyl-4-hydroxyhydrocinnamoyl(hydrazide, and N,N'-bis-[2-(3,5-t-butyl-4-hydroxyhydroxocinnamoyl oxy)-ethyl]-oxamide, and preferably neopentanetetrayltetrakis (3,5-di-t-butyl-4-hydroxyhydrocinnamate), n-octadecyl-3,5-di-t-butyl-4-hydroxyhydrocinnamate, 1,3,5-trimethyl-2,4,6-tris(3,5-di-t-butyl-4-hydroxy-benzyl)benzene, 1,3,5-tris-(3,5-di-t-butyl-4-hydroxybenzyl)isocyanurate, 2,6-di-t-butyl-p-cresol or 2,2'-ethylidene-bis(4,6-di-t-butylphenol).

(12) Lactones, for example, 5,7-di-t-butyl-3-phenyl-3H-benzofuran-2-one;
5,7-di-cumyl-3-phenyl-3H-benzofuran-2-one; nonyl-e-phenyl-3H-benzofuran-2-one; dinonyl-3-phenyl-3H-benzofuran-2-one;
5-t-butyl-3-phenyl-3H-benzofuran-2-one;
5-cumyl-3-phenyl-3H-benzofuran-2-one; and octyl-3-phenyl-3H-benzofuran-2-one, and other 3-arylbenzofuran-2-ones.

Other additives, such as oxazapholidines, may additionally or alternatively be present. Likewise, the instant compounds prevent color formation when hindered amine light stabilizers are present, such hindered amines including-bis(1,2,2,6,6-pentamethyl-4-piperidyl)2-n-butyl-2-(3,5-di-t-butyl-4-hydroxy-benzyl) malonate; bis(2,2,6,6-tetramethyl-4-piperidyl) sebacate; dimethyl-succinate polymer with 4-hydroxy-2,2,6,6-tetramethyl-1-piperidinethanol; and polymers of 2,4-dichloro-6-octylamino-s-triazine with N'-(2,2,6,6-tetramethyl-4-piperidyl)hexamethylene diamine.

Thus, what has been shown is that one way to reduce the formation of volatile phenol is to substitute at least a portion of the phosphite additive with a phosphite which does not break down into a phenolic unit or minimally breaks down into phenolic units. Preferred examples of this type of phosphite include ethoxy-paracumylphenyl diisodecyl phosphite, propoxy-paracumylphenyl diisodecyl phosphite, para-cumyl phenyl diisodecyl phosphite and bis para-cumyl isodecyl phosphite as well as more generically, formulas (I) and (II).

More generally disclosed is a process for reducing the emission of phenol in a polymer resin which comprises replacing at least a portion of a phosphite additive which releases phenol upon exposure to heat with a phosphite composition selected from the group consisting of formula (I)

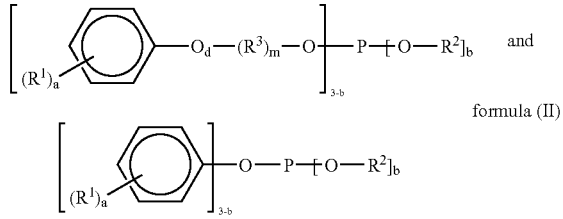

wherein
$R^1$ is

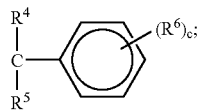

$R^2$ is selected from the group consisting of $C_{8-16}$ alkyls;
$R^3$ is selected from the group consisting of $C_{1-4}$ alkyls;
m is an integral value ranging from 0 to 1 inclusive;
a is an integral value ranging from 1 to 4 inclusive;
b is an integral value ranging from 1 to 2 inclusive;
$R^4$ and $R^5$ are independently selected from the group consisting of $C_{1-3}$ alkyls,
$R^6$ is selected from the group consisting of $C_{8-12}$ alkyls and $C_{8-12}$ alkoxy compounds;
c is an integral value ranging from 0 to 4 inclusive; and
d is equal to m.

This invention has been described in detail with reference to specific embodiments thereof, including the respective best modes for carrying out each embodiment. It shall be understood that these illustrations are by way of example and not by way of limitation.

The invention claimed is:

1. A process for reducing phenol emissions from a polymer resin comprising the step of adding at least one phosphite additive of formula (I) to said resin, wherein said formula (I) comprises:

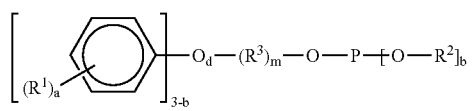

wherein
$R^1$ is

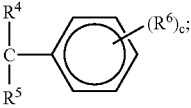

$R^2$ is selected from the group consisting of $C_{8-16}$ alkyls;
$R^3$ is selected from the group consisting of $C_{1-4}$ alkylenes;
m is 1;
a is an integral value ranging from 1 to 4 inclusive;
b is an integral value ranging from 1 to 2 inclusive; and
$R^4$ and $R^5$ are independently selected from the group consisting of $C_{1-3}$ alkyls;
$R^6$ is selected from the group consisting of $C_{8-12}$ alkyls and $C_{8-12}$ alkoxy compounds;
c is an integral value ranging from 0 to 4 inclusive; and
d is equal to m.

2. The process of claim 1 wherein
$R^2$ is $C_{10}H_{21}$;
$R^3$ is selected from the group consisting of ethylene and propylene;
a is 1;
$R^4$ and $R^5$ are methyl;
c is 0; and
d is 1.

3. The process of claim 2 wherein
$R^1$ is

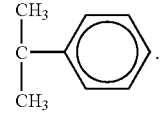

4. The process of claim 3 wherein said phosphite is selected from the group consisting of ethoxy-paracumylphenyl diisodecyl phosphite and propoxy-paracumylphenyl diisodecyl phosphite.

5. The process of claim 4 wherein said polymer resin is a halogenated resin.

6. The process of claim 5 wherein said halogenated resin is polyvinyl chloride.

7. A process for reducing phenol emissions from a polymer resin comprising the step of adding at least one phosphite additive of formula (II) to said resin, wherein said formula (II) comprises:

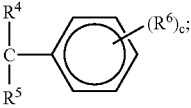

wherein
$R^1$ is selected from the group consisting of $C_{8-12}$ alkyls and $C_{8-12}$ alkoxy compounds;
$R^2$ is selected from the group consisting of $C_{8-16}$ alkyls;
a is an integral value ranging from 1 to 4 inclusive; and
b is an integral value ranging from 1 to 2 inclusive.

8. The process of claim 7 wherein

R$^2$ is C$_{10}$H$_{21}$; and a is 1.

9. The process of claim 7 wherein said phosphite is selected from the group consisting of nonylphenyl diisodecyl phosphite, di-nonylphenyl dilsodecyl phosphite, bis(nonylphenyl) isodecyl phosphite and bis(di-nonylpnenyl)isodecyl phosphite.

10. The process of claim 7 wherein said polymer resin is a halogenated resin.

11. The process of claim 10 wherein said halogenated resin is polyvinyl chloride.

12. A process for reducing phenol emissions from a polymer resin comprising the step of adding at least one phosphite additive to said resin, said at least one phosphite selected from the group consisting of formulas (I) and (II)

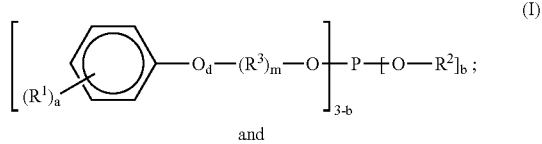

and

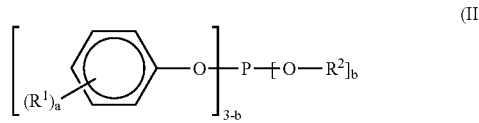

wherein

R$^1$ is

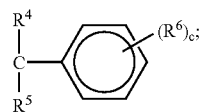

R$^2$ is selected from the group consisting of C$_{8-16}$ alkyls;

R$^3$ is selected from the group consisting of C$_{1-4}$ alkylenes;

m is 1;

a is an integral value ranging from 1 to 4 inclusive;

b is an integral value ranging from 1 to 2 inclusive;

R$^4$ and R$^5$ are independently selected from the group consisting of C$_{1-3}$ alkyls;

R$^6$ is selected from the group consisting of C$_{8-12}$ alkyls and C$_{8-12}$ alkoxy compounds;

c is an integral value ranging from 0 to 4 inclusive; and d is equal to m.

13. The process of claim 12 wherein

R$^2$ is C$_{10}$H$_{21}$;

R$^3$ is selected from the group consisting of ethylene and propylene;

a is 1;

R$^4$ and R$^5$ are methyl;

c is 0; and d is 1.

14. The process of claim 13 wherein

R$^1$ is

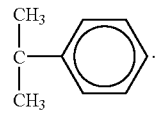

15. The process of claim 14 wherein said phosphite is selected from the group consisting of ethoxy-paracumylphenyl diisodecyl phosphite, and propoxy-paracumylphenyl diisodecyl phosphite.

16. The process of claim 12 wherein said polymer resin is a halogenated resin.

17. The process of claim 16 wherein said halogenated resin is polyvinyl chloride.

18. A process for reducing the emission of phenol from a polymer resin which comprises replacing at least a portion of a phosphite additive which emits phenol from said resin with a phosphite composition selected from the group consisting of formula (I)

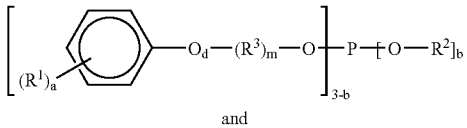

and formula (II)

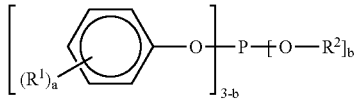

wherein

R$^1$ is

R$^2$ is selected from the group consisting of C$_{8-16}$ alkyls;

R$^3$ is selected from the group consisting of C$_{1-4}$ alkylenes;

m is 1;

a is an integral value ranging from 1 to 4 inclusive;

b is an integral value ranging from 1 to 2 inclusive;

R$^4$ and R$^5$ are independently selected from the group consisting of C$_{1-3}$ alkyls;

R$^6$ is selected from the group consisting of C$_{8-12}$ alkyls and C$_{8-12}$ alkoxy compounds;

c is an integral value ranging from 0 to 4 inclusive; and d is equal to m.

19. The process of claim 18 wherein

R$^2$ is C$_{10}$H$_{21}$;

R$^3$ is selected from the group consisting of ethylene and propylene;

a is 1;

R$^4$ and R$^5$ are methyl;

c is 0; and d is 1.

20. The process of claim 19 wherein $R^1$ is

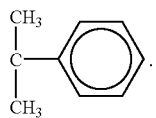

21. The process of claim 20 wherein said phosphite is selected from the group consisting of ethoxy-paracumylphenyl diisodecyl phosphite and propoxy-paracumylphenyl diisodecyl phosphite.

22. The process of claim 18 wherein said polymer resin is a halogenated resin.

23. The process of claim 22 wherein said halogenated resin is polyvinyl chloride.

* * * * *

UNITED STATES PATENT AND TRADEMARK OFFICE
CERTIFICATE OF CORRECTION

PATENT NO. : 7,470,735 B2
APPLICATION NO. : 10/709578
DATED : December 30, 2008
INVENTOR(S) : Stevenson et al.

Page 1 of 1

It is certified that error appears in the above-identified patent and that said Letters Patent is hereby corrected as shown below:

In column 19, claim 1 – the proper formula is

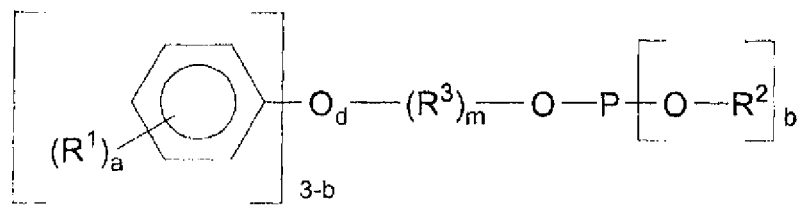

In column 21, claim 9, row 7 the word "dislsodecyl" – should be "diisodecyl"

Signed and Sealed this

Seventh Day of April, 2009

JOHN DOLL
*Acting Director of the United States Patent and Trademark Office*